United States Patent
Castro et al.

(10) Patent No.: US 9,943,688 B2
(45) Date of Patent: Apr. 17, 2018

(54) WIRELESS VISUAL PROSTHESIS WITH REMOTE DRIVER AND COIL

(75) Inventors: Richard Agustin Castro, Pasadena, CA (US); Robert J. Greenberg, Los Angeles, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 0 days.

(21) Appl. No.: 13/163,506

(22) Filed: Jun. 17, 2011

(65) Prior Publication Data

US 2011/0313486 A1 Dec. 22, 2011

Related U.S. Application Data

(60) Provisional application No. 61/356,492, filed on Jun. 18, 2010.

(51) Int. Cl.
- A61F 9/08 (2006.01)
- A61N 1/36 (2006.01)
- G01R 33/48 (2006.01)
- A61N 1/08 (2006.01)

(52) U.S. Cl.
CPC .......... *A61N 1/36046* (2013.01); *A61N 1/086* (2017.08); *G01R 33/4806* (2013.01)

(58) Field of Classification Search
USPC ..................................................... 607/53–54
See application file for complete search history.

(56) References Cited

U.S. PATENT DOCUMENTS

| | | | |
|---|---|---|---|
| 5,109,844 A | 5/1992 | de Juan, Jr. et al. | |
| 5,594,498 A * | 1/1997 | Fraley | 348/158 |
| 5,935,155 A | 8/1999 | Humayun et al. | |
| 6,400,989 B1 | 6/2002 | Eckmiller | |
| 6,458,157 B1 | 10/2002 | Suaning | |
| 7,623,930 B2 * | 11/2009 | Zeijlemaker et al. | 607/60 |
| 2003/0206019 A1 * | 11/2003 | Boskamp | 324/322 |
| 2008/0058897 A1 * | 3/2008 | McMahon et al. | 607/54 |
| 2008/0082147 A1 * | 4/2008 | Dai | A61N 1/3787 607/61 |
| 2008/0097548 A1 * | 4/2008 | Greenberg et al. | 607/54 |
| 2011/0022123 A1 * | 1/2011 | Stancer et al. | 607/60 |

* cited by examiner

*Primary Examiner* — Carl H Layno
*Assistant Examiner* — Jennifer Ghand
(74) *Attorney, Agent, or Firm* — Scott Dunbar

(57) ABSTRACT

The present invention is wireless visual prosthesis with a remote driver for the external coils this, among other things, provides for a magnetic resonance image (MRI) safe visual prosthesis. fMRI is an effective tool for analyzing cortical responses to neural stimulation, such as from a visual prosthesis. However, the external electronics of a visual prosthesis cannot operate in a MRI field. The present invention provides a radio frequency shielded link between a video processing unit, driver circuitry and the coils used for communicating with the implantable portion of the visual prosthesis.

25 Claims, 7 Drawing Sheets

WIRELESS VISUAL PROSTHESIS WITH REMOTE DRIVER AND COIL

CROSS REFERENCE TO RELATED APPLICATIONS

The present application is related to, and claims priority to U.S. Provisional Application No. 61/356,492 entitled "Development of Methods for fMRI in Retinal Prosthesis", filed on Jun. 18, 2010, which is incorporated herein by reference in its entirety.

FIELD OF THE INVENTION

The present invention is generally directed to neural stimulation and more specifically to adaptations necessary to operate a visual prosthesis with a remote driver and coil, and more specifically to operation of visual prosthesis in an fMRI field.

BACKGROUND OF THE INVENTION

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising prostheses for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparati to aid the visually impaired. Specifically, great effort has been expended in the area of intraocular retinal prosthesis devices in an effort to restore vision in cases where blindness is caused by photoreceptor degenerative retinal diseases; such as retinitis pigmentosa and age related macular degeneration which affect millions of people worldwide.

Present studies have been performed on use of retinal prostheses to restore partial sight to people blinded by outer retinal degenerative diseases. Diseases such as retinitis pigmentosa destroy photoreceptors but leave a significant percentage of inner-retinal cells (ganglion and bipolar cells) intact and functional. Direct electrical stimulation of inner-retinal cells via an implanted array of electrodes may provide vision.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the sensory information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the visual neurons, control the electronic field distribution and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 µA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal electrode array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

SUMMARY OF THE INVENTION

The present invention is wireless visual prosthesis with a remote driver for the external coils this, among other things, provides for a magnetic resonance image (MRI) safe visual prosthesis. fMRI is an effective tool for analyzing cortical responses to neural stimulation, such as from a visual prosthesis. However, the external electronics of a visual prosthesis cannot operate in a MRI field. The present invention provides a radio frequency shielded link between a video processing unit, driver circuitry and the coils used for communicating with the implantable portion of the visual prosthesis.

A first aspect of the invention is a visual prosthesis including a video processing unit providing stimulation signals, a primary coil transmitting the stimulation signals, a radio frequency shielded link connecting the video processing unit to the primary coil and separating the video processing unit from a controlled environment, an implantable neural stimulator suitable to operate within the controlled environment; and an implantable coil electrically connected to the implantable neural stimulator receiving stimulation signals from the primary coil.

A second aspect of the invention is the visual prosthesis of the first aspect where the controlled environment is a magnetic resonance imaging field (MRI), a positron emission tomography (PET) field, a magnetoencephalography (MEG) field, or an electroencephalography field (EEG), or other means of measuring cortical activity that requires a controlled electromagnetic field.

A third aspect of the invention is the visual prosthesis of the first aspect, including a driver connected to a coaxial cable which is connected to tuned circuit which is connected to a coil.

A fourth aspect of the invention is the visual prosthesis of the third aspect further including a non-ferrite core coil in the tuned circuit.

A fifth aspect of the invention is the visual prosthesis of the first aspect including a bidirectional shielded link providing for back telemetry data returned to the video processing unit.

A sixth aspect of the invention is the visual prosthesis of the fifth aspect further including a low noise amplifier in the back telemetry link.

A seventh aspect of the invention is a visual prosthesis including a video processing unit providing stimulation signals, a primary coil transmitting the stimulation signals, a radio frequency shielded link greater than one foot in length connecting the video processing unit to the primary coil, an implantable neural stimulator; and a implantable coil electrically connected to the implantable neural stimulator receiving stimulation signals from the primary coil.

An eighth aspect of the invention is a method of fitting a visual prosthesis using the visual prosthesis of the first aspect of the invention including the steps of stimulating neural tissue, measuring cortical responses to the stimulation of neural tissue, and adjusting the visual prosthesis according to the measurements of cortical responses.

BRIEF DESCRIPTION OF THE DRAWINGS

The accompanying drawings, which are incorporated into and constitute a part of this specification, illustrate one or more embodiments of the present disclosure and, together with the description of example embodiments, serve to explain the principles and implementations of the disclosure.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
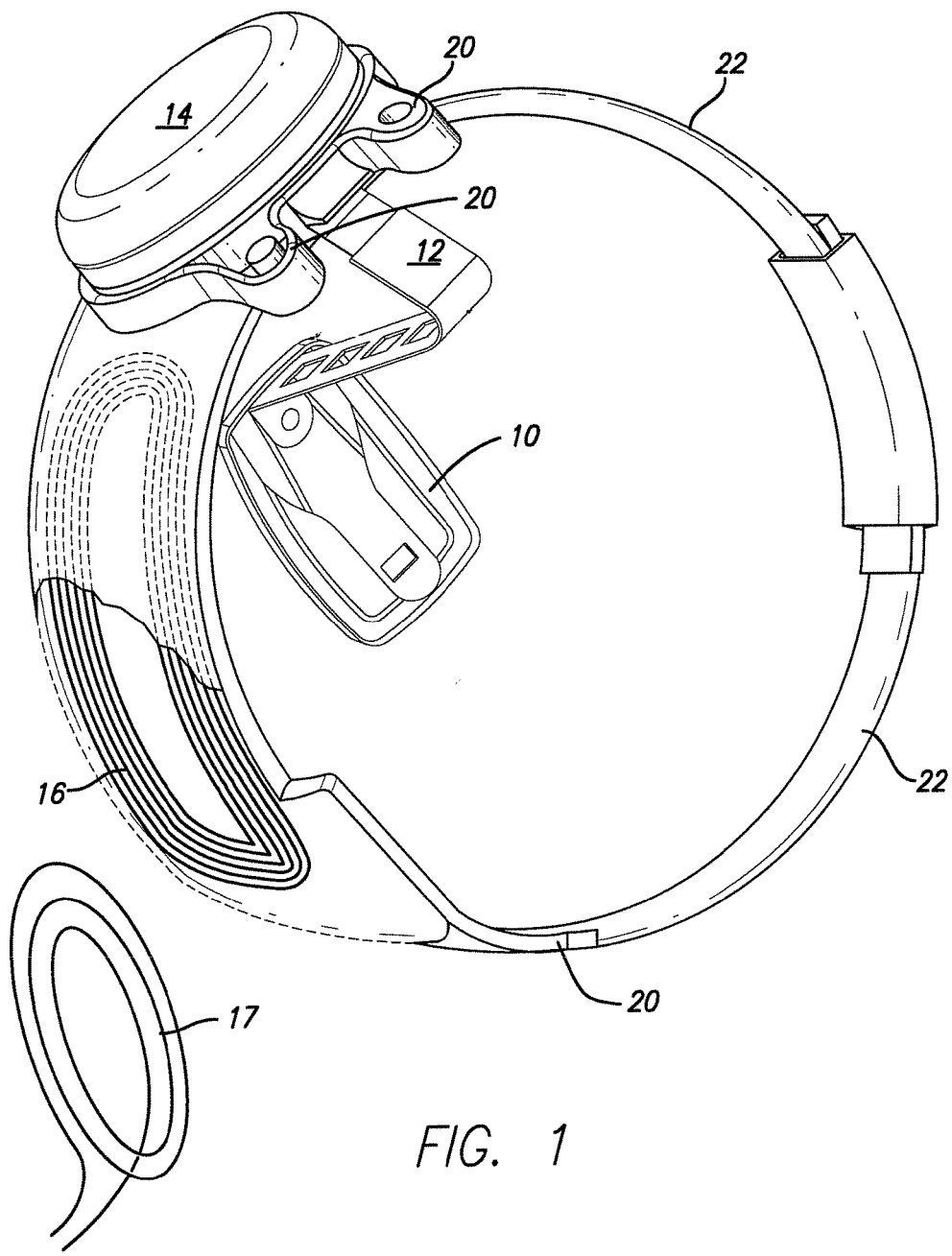
FIG. 1 is a perspective view of the implantable portion of the preferred retinal prosthesis.
Figure 2:
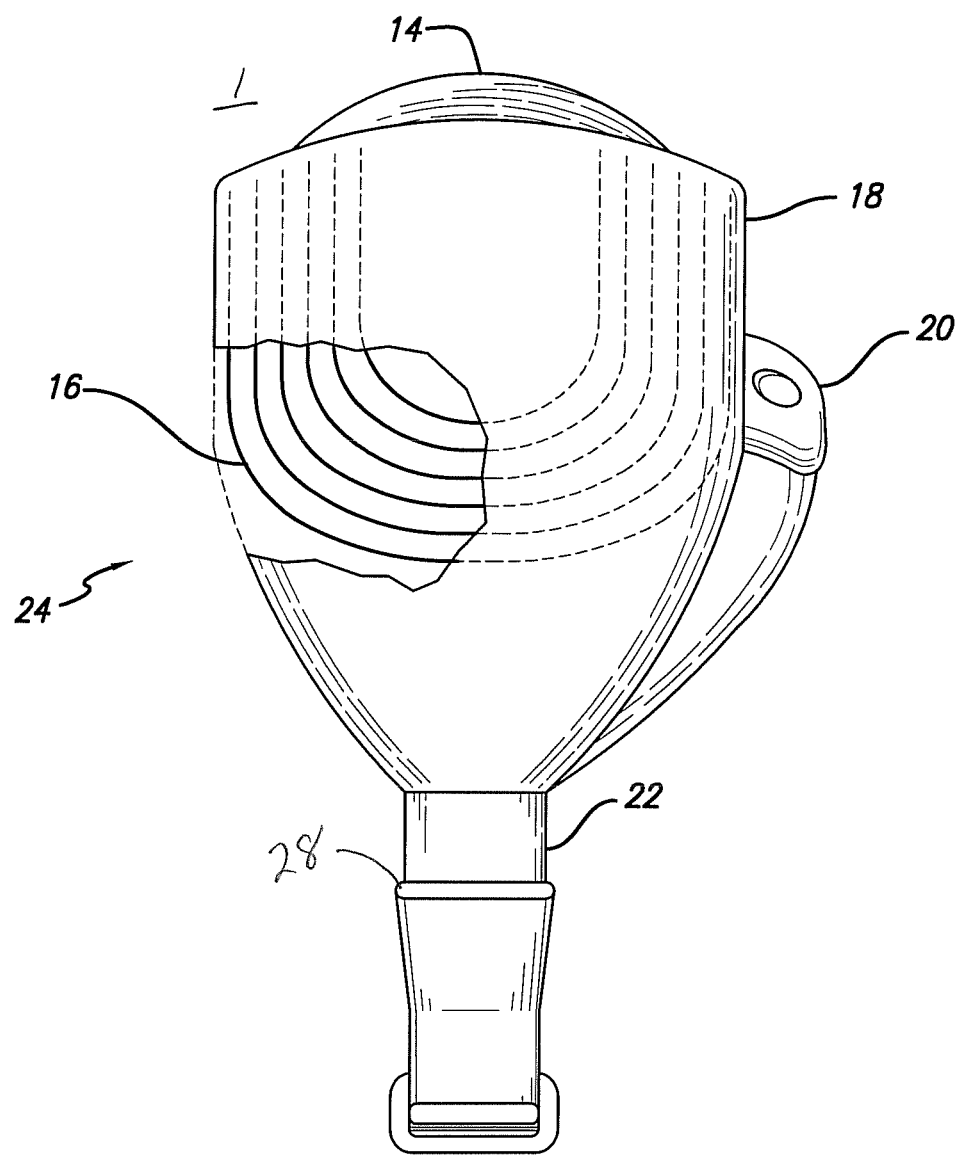
FIG. 2 is a side view of the implantable portion of the preferred retinal prosthesis showing the strap fan tail in more detail.

FIGS. 1 and 2 present the general structure of a visual prosthesis used in implementing the invention.

FIG. 1 shows a perspective view of the implantable portion of the preferred retinal prosthesis. A flexible circuit 12 includes a flexible circuit electrode array 10 which is mounted by a retinal tack (not shown) or similar means to the epiretinal surface. The flexible circuit electrode array 10 is electrically coupled by a flexible circuit cable 12, which pierces the sclera and is electrically coupled to an electronics package 14, external to the sclera.

The electronics package 14 is electrically coupled to an implantable inductive coil 16. Preferably the implantable inductive coil 16 is made from wound wire. Alternatively, the implantable inductive coil 16 may be made from a flexible circuit polymer sandwich with wire traces deposited between layers of flexible circuit polymer. The implanted inductive coil receives power and data from an external inductive coil 17, which is external to the body. The electronics package 14 and implantable inductive coil 16 are held together by the molded body 18. The molded body 18 holds the electronics package 14 and implantable inductive coil 16 end to end. The implantable inductive coil 16 is placed around the electronics package 14 in the molded body 18. The molded body 18 holds the implantable inductive coil 16 and electronics package 14 in the end to end orientation and minimizes the thickness or height above the sclera of the entire device. The molded body 18 may also include suture tabs 20. The molded body 18 narrows to form a strap 22 which surrounds the sclera and holds the molded body 18, implantable inductive coil 16, and electronics package 14 in place. The molded body 18, suture tabs 20 and strap 22 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The implantable inductive coil 16 and molded body 18 are preferably oval shaped. A strap 22 can better support an oval shaped coil. It should be noted that the entire implant is attached to and supported by the sclera. An eye moves constantly. The eye moves to scan a scene and also has a jitter motion to improve acuity. Even though such motion is useless in the blind, it often continues long after a person has lost their sight. By placing the device under the rectus muscles with the electronics package in an area of fatty tissue between the rectus muscles, eye motion does not cause any flexing which might fatigue, and eventually damage, the device. It should be noted that the visual prosthesis of the present invention provides for bidirectional data. Hence the inductive coils 16 and 17 may be coil pairs, one each for transmitting and receiving.

FIG. 2 shows a side view of the implantable portion of the retinal prosthesis, in particular, emphasizing the fan tail 24. When implanting the retinal prosthesis, it is necessary to pass the strap 22 under the eye muscles to surround the sclera. The implantable inductive coil 16 and molded body 18 must also follow the strap 22 under the lateral rectus muscle on the side of the sclera. The implantable portion of the retinal prosthesis is very delicate. It is easy to tear the molded body 18 or break wires in the implantable inductive coil 16. In order to allow the molded body 18 to slide smoothly under the lateral rectus muscle, the molded body 18 is shaped in the form of a fan tail 24 on the end opposite the electronics package 14. The strap 22 further includes a hook 28 the aids the surgeon in passing the strap under the rectus muscles.

Figure 3:
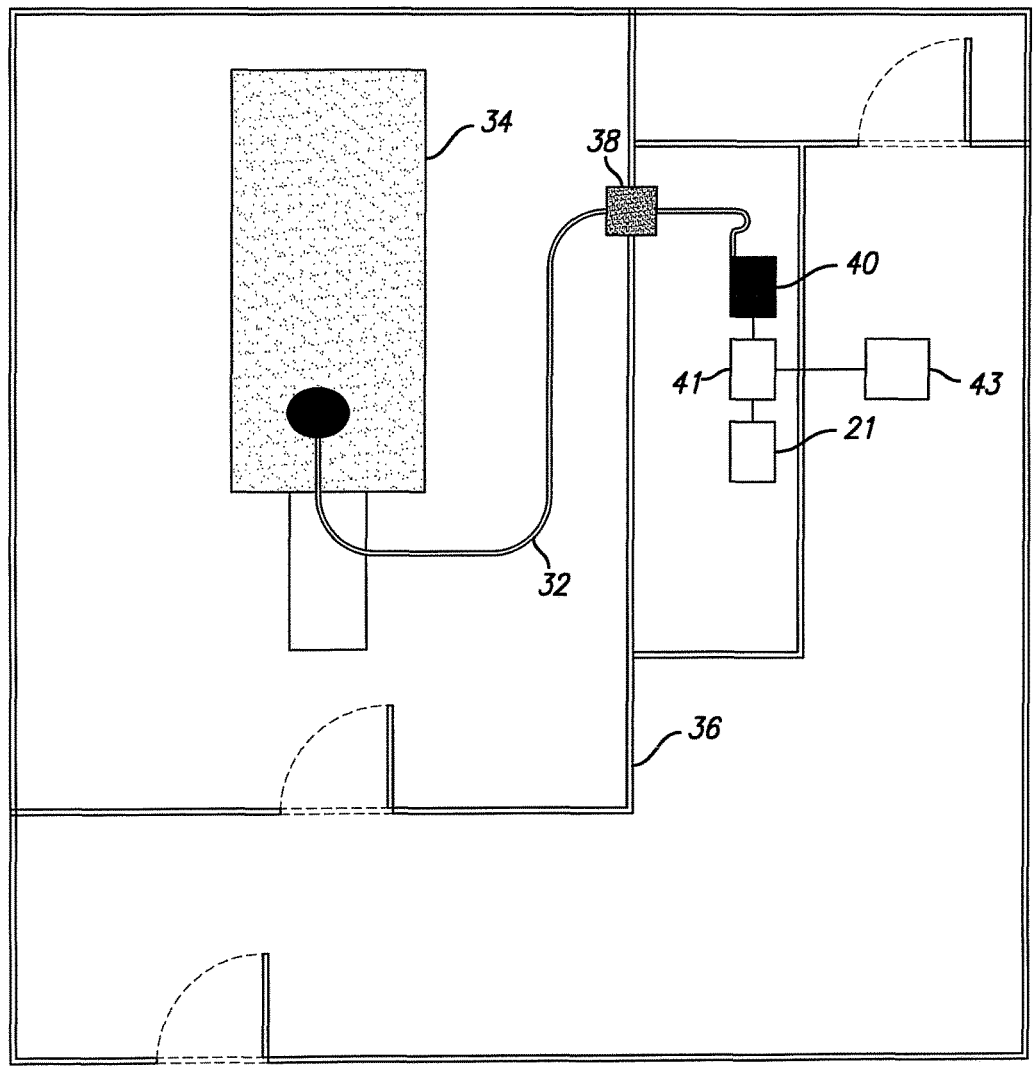
FIG. 3 is a diagram showing application of the invention in a typical fMRI setup.

The preferred embodiment of the invention is used to separate the visual prosthesis electronics from a controlled environment. The controlled environment may be a functional magnetic resonance imaging system (fMRI), a positron emission tomography imaging system (PET), magnetoencephalography (MEG), electroencephalography (EEG), or other means of measuring cortical activity that requires a controlled electromagnetic field around the head of the patient. Referring to FIG. 3, the patient is placed in an fMRI scanner 34, after being implanted with the implantable portion of a visual prosthesis, as shown in FIGS. 1 and 2. The external coil 17 is attached to a coaxial cable 32 which extends out of the controlled environment 36 through an RF shield port 38. The coaxial cable 32 is attached to driver circuitry 40. Driver circuitry 40 is connected to an interface board 41. The interface board 41 connects to both the video processing unit 21 and a control computer 43. The control computer 43 may in turn interface with the control for the fMRI scanner to provide feedback for fitting the visual prosthesis.

Figure 4:
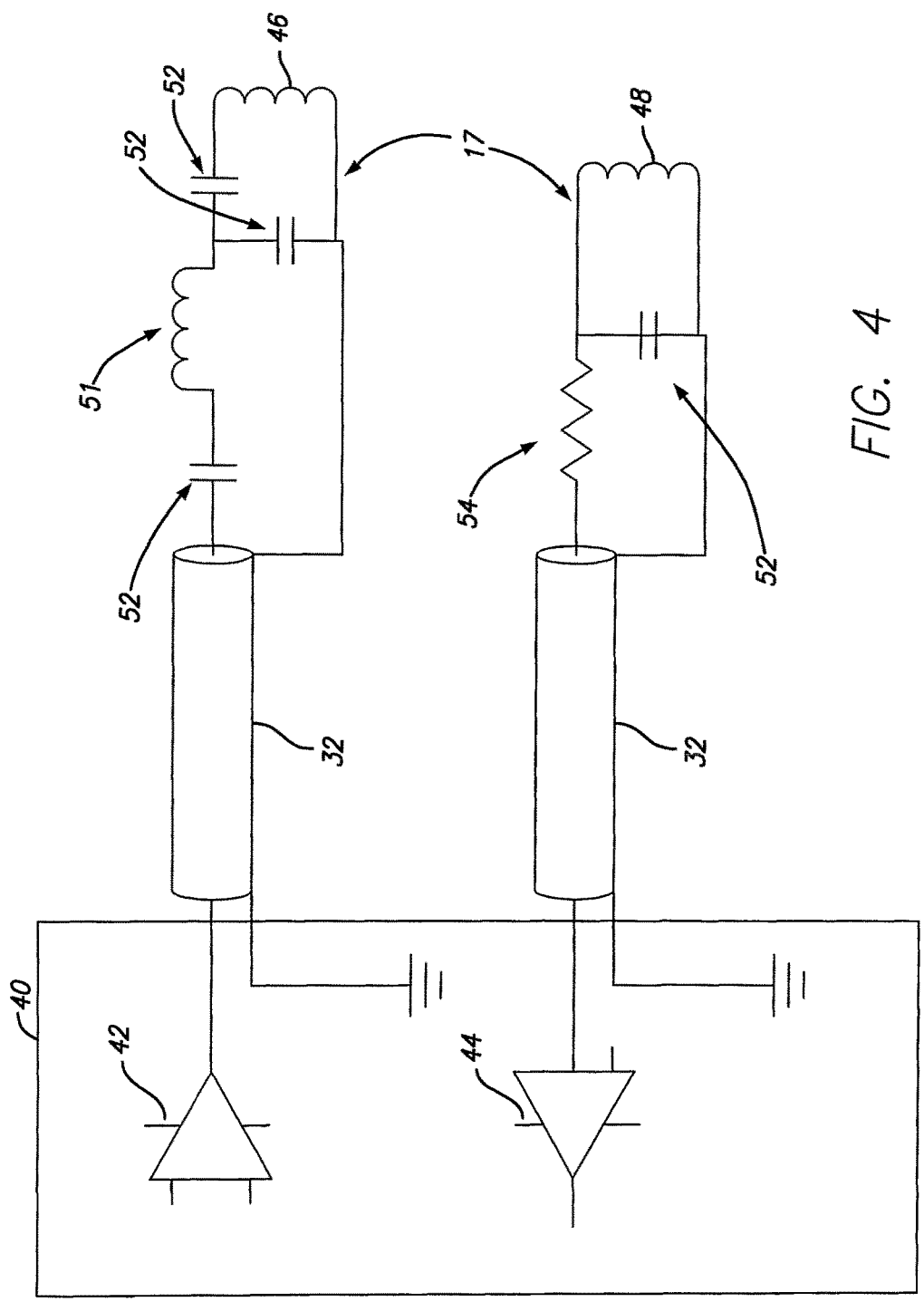
FIG. 4 is a schematic diagram of the link between the video processing unit and the telecommunications coils.

Referring to FIG. 4, the RF shielded link is shown in more detail. Outside the controlled environment 36, the coaxial cables 32, are connected to driver electronics 40, which includes a power amplifier 42 for forward stimulation data and low noise amplifier 44 for back telemetry data. What is shown as an external coil 17 in FIG. 1 is two coils, a stimulation data primary coil 46 and a back telemetry receiving coil 48. The tuning circuits between the coaxial cables 32 and the external coils 17 must be compatible with the controlled environment. The inductor 51 would be more efficient with a ferrite core, but is provided with a non-ferrite core to be compatible with the controlled environment 36. The circuits are tuned by capacitors 52 which are compatible with the controlled environment 36. A resistor 54 is added to balance the impedance of the coaxial cable 32 in the back telemetry circuit as the back telemetry signal is very weak.

Alternatively, the present invention may be helpful independently of use in a controlled environment. In the prior art, the external coils and driver circuitry are mounted to a pair of glasses (see FIG. 6). Mounting the driver circuitry close to the coils is more efficient and reduces electromagnetic interference. However, the resulting glasses are quite heavy. It is advantageous to use the present invention to move the driver circuitry to the video processing unit thereby reducing the weight of the glasses.

Figure 5:
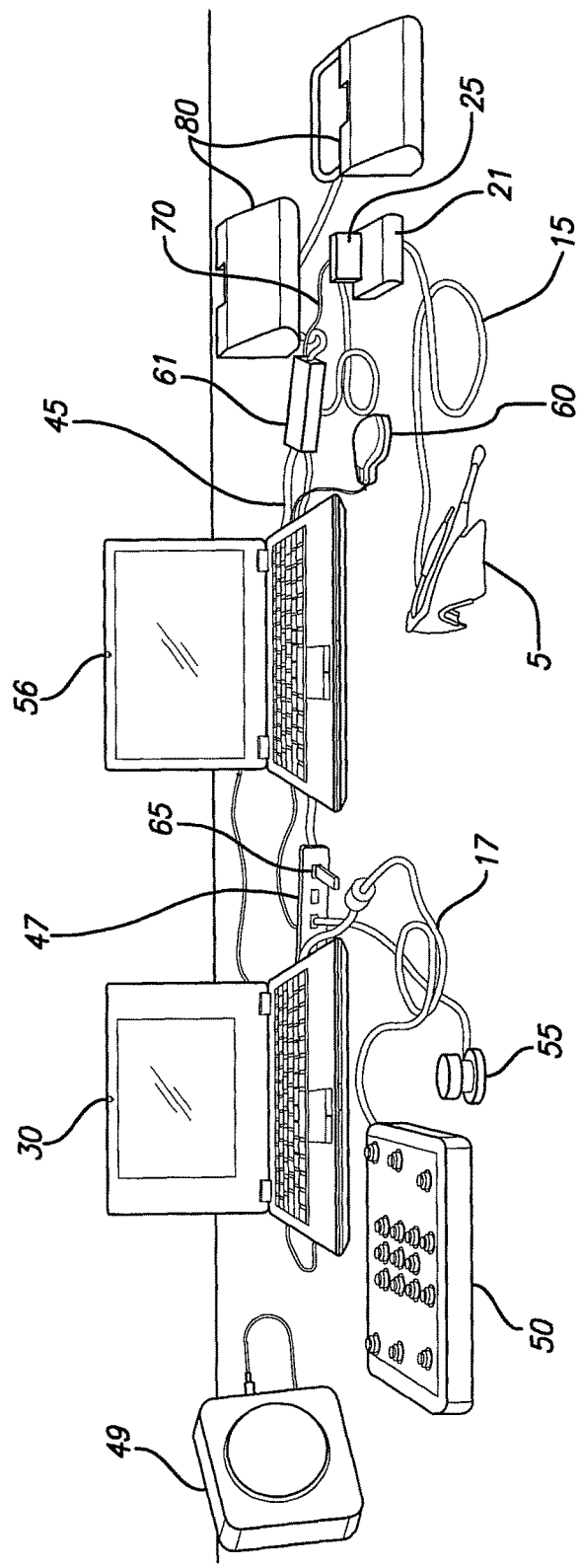
FIG. 5 shows the components of the visual prosthesis system.

Referring to FIG. 5, a Fitting System (FS) may be used to configure and optimize the visual prosthesis of the Retinal Stimulation System. The present invention is useful in fitting a visual prosthesis. The process is to place the patient in an fMRI scanner, stimulate visual neurons using the visual prosthesis, measure cortical response to the stimulation and adjust the visual prosthesis according to the measured cortical response. This allows for the visual prosthesis to be fit automatically without requiring patent feedback.

The Fitting System may comprise custom software with a graphical user interface (GUI) running on a dedicated laptop computer 56. Within the Fitting System are modules for performing diagnostic checks of the implant, loading and executing video configuration files, viewing electrode voltage waveforms, and aiding in conducting psychophysical experiments. A video module can be used to download a video configuration file to a Video Processing Unit (VPU) 21 and store it in non-volatile memory to control various aspects of video configuration, e.g. the spatial relationship between the video input and the electrodes. The software can also load a previously used video configuration file from the VPU 21 for adjustment.

The Fitting System can be connected to the Psychophysical Test System (PTS), located for example on a dedicated laptop 30, in order to run psychophysical experiments. In psychophysics mode, the Fitting System enables individual electrode control, permitting clinicians to construct test stimuli with control over current amplitude, pulse-width, and frequency of the stimulation. In addition, the psychophysics module allows the clinician to record subject responses. The PTS may include a collection of standard psychophysics experiments developed using for example MATLAB (MathWorks) software and other tools to allow the clinicians to develop customized psychophysics experiment scripts.

Any time stimulation is sent to the VPU 21, the stimulation parameters are checked to ensure that maximum charge per phase limits, charge balance, and power limitations are met before the test stimuli are sent to the VPU 21 to make certain that stimulation is safe.

Using the psychophysics module, important perceptual parameters such as perceptual threshold, maximum comfort level, and spatial location of percepts may be reliably measured.

Based on these perceptual parameters, the fitting software enables custom configuration of the transformation between video image and spatio-temporal electrode stimulation parameters in an effort to optimize the effectiveness of the retinal prosthesis for each subject.

The Fitting System laptop 56 is connected to the VPU 21 using an optically isolated Communications Adaptor 61. Because it is optically isolated, the serial connection adapter 61 assures that no electric leakage current can flow from the Fitting System laptop 56.

As shown in FIG. 5, the following components may be used with the Fitting System according to the present disclosure. A Video Processing Unit (VPU) 21 for the subject being tested, a Charged Battery 25 for VPU 21, Glasses 5, a Fitting System (FS) Laptop 56, a Psychophysical Test System (PTS) Laptop 30, a PTS CD (not shown), a Communication Adapter (CA) 61, a USB Drive (Security) (not shown), a USB Drive (Transfer) (not shown), a USB Drive (Video Settings) (not shown), a Patient Input Device (RF Tablet) 50, a further Patient Input Device (Jog Dial) 55, Glasses Cable 15, CA-VPU Cable 70, CFS-CA Cable 45, CFS-PTS Cable, Four (4) Port USB Hub 47, Mouse 60, LED Test Array 80, Archival USB Drive 49, an Isolation Transformer (not shown), adapter cables (not shown), and an External Monitor (not shown).

The external components of the Fitting System according to the present disclosure may be configured as follows. The battery 25 is connected with the VPU 21. The PTS Laptop 30 is connected to FS Laptop 56 using the CFS-PTS Cable. The PTS Laptop 30 and FS Laptop 56 are plugged into the Isolation Transformer (not shown) using the Adapter Cables (not shown). The Isolation Transformer is plugged into the wall outlet. The four (4) Port USB Hub 47 is connected to the FS laptop 56 at the USB port. The mouse 60 and the two Patient Input Devices 50 and 55 are connected to four (4) Port USB Hubs 47. The FS laptop 56 is connected to the Communication Adapter (CA) 61 using the CFS-CA Cable 45. The CA 61 is connected to the VPU 21 using the CA-VPU Cable 70. The Glasses 5 are connected to the VPU 21 using the Glasses Cable 15.

Figure 6A:
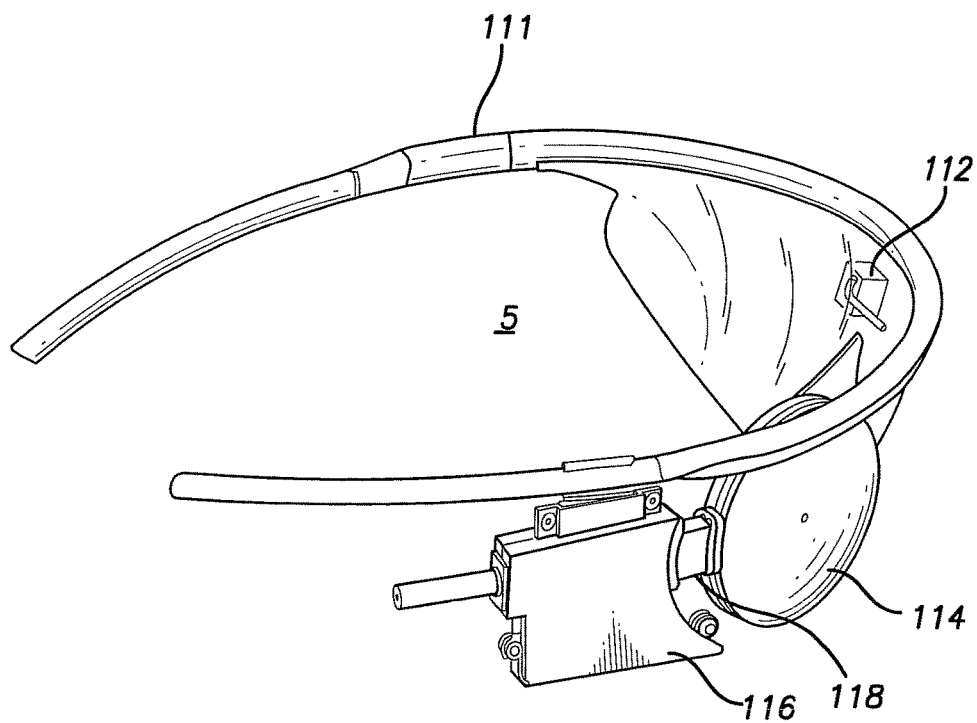
FIG. 6A shows a side view of an exemplary pair of glasses for capturing and transmitting video information.
Figure 6B:
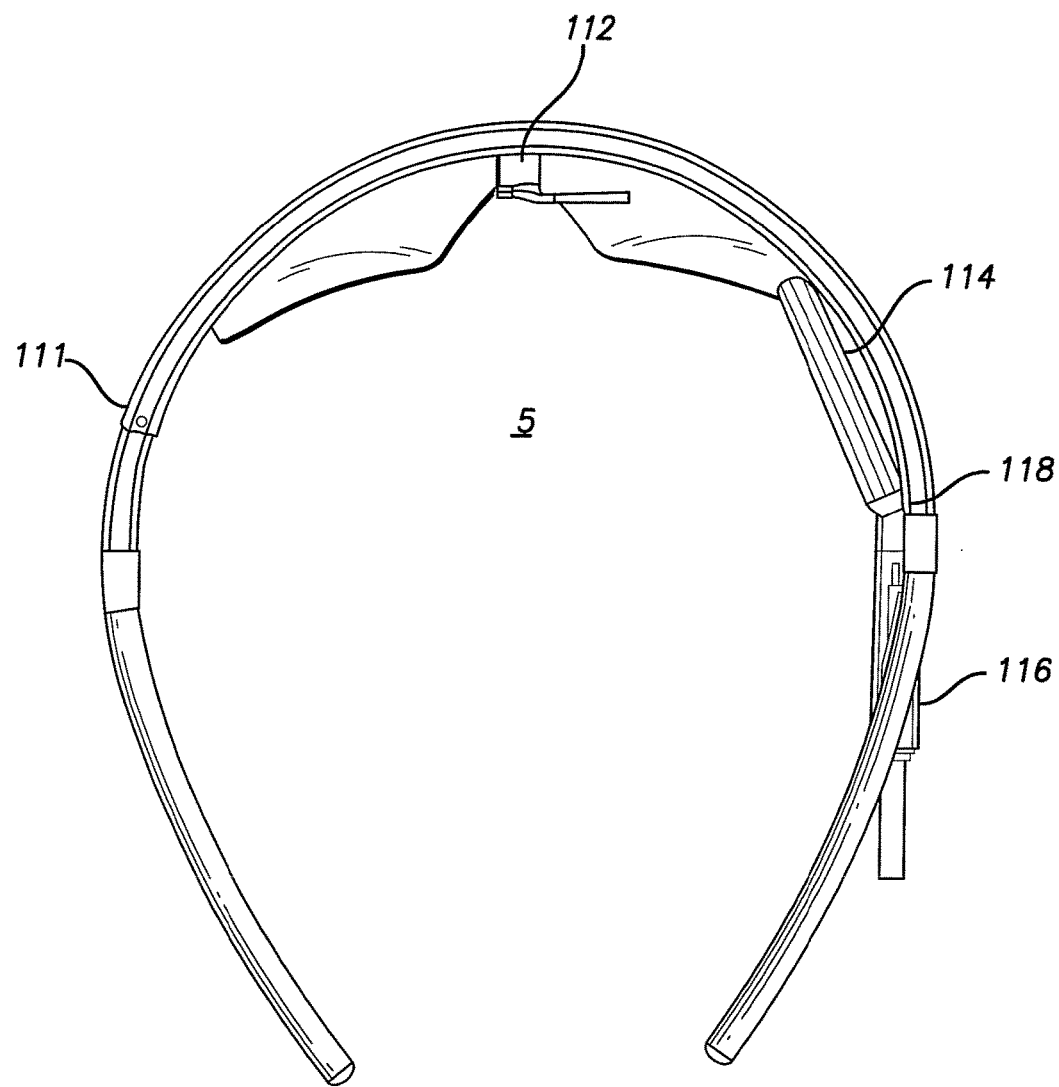
FIG. 6B shows a top view of the exemplary pair of glasses shown in FIG. 6A.

FIG. 6A shows a side view of an exemplary pair of glasses 5 for capturing and transmitting video information. The pair of glasses 5 can comprise, for example, a frame 111 for holding a video camera 112, an external coil 114, and a mounting system 116 for the external coil 114. The mounting system 116 may also enclose the RF circuitry. In this configuration, the video camera 112 captures live video. The video signal can be sent, for instance, to an external VPU 21 shown in FIG. 5, which processes the video signal and subsequently transforms the processed video signal into electrical stimulation patterns or data. The electrical stimulation data are then sent to the external coil 114 which sends both the data and power via radio-frequency (RF) telemetry to an implantable portion of the retinal prosthesis (such as a receiving coil in the retinal prosthesis) and/or an external testing unit for testing/measuring of the data and power received from the external coil 114. FIG. 6B shows a top view of the exemplary pair of glasses.

Video Configuration Information

Video processing can be configured using a collection of settings known as video configuration information. This information can be dynamically set by the host. It includes a spatial map, a brightness map color map, timing profiles, and Image Presentation Rate/Stimulation Frequency and zoom settings.

The spatial map is used by the video filters when processing the raw video image. The spatial map can contain one pixel location for every electrode and assume a 12×20 raw video image. A possible application programming interface (API) can be defined as follows:

```
#define ELECTRODE_NUM (60)
typedef struct {
    unsigned short columnPosition;      // column 0 - 19
    unsigned short rowPosition;         // row 0 - 11
```

The brightness map is used by the telemetry engine video manager, later discussed, to translate the filtered video image brightness levels to driver amplitude values. For each brightness level, an electrode can have a unique corresponding driver amplitude value. There can be one driver amplitude range that is used for all electrodes.

```
#define BRIGHTNESS_LEVELS
unsigned short brightnessMap[ELECTRODE_NUM][BRIGHTNESS_LEVELS];
unsigned short globalAmplitudeRange;
```

According to one embodiment of the present disclosure, there are six timing profiles that can be configured. Each electrode associates one of the six profiles with its anodic pulse, and one of the six for its cathodic pulse.

```
#define PROFILE_NUM
typedef struct {
    unsigned short start;
    unsigned short stop;
} profile;
profile timingProfiles[PROFILE_NUM];
typedef struct {
    unsigned short anodicProfile;
    unsigned short cathodicProfile;
} profile Choice;
profileChoice electrodeProfileSelection[ELECTRODE_NUM];
```

As to the video filter settings, the filter processor can be configured to perform a reverse video filter in conjunction with a Difference of Gaussians (DoG) filter.

```
struct {
    int reverseVideoOn;               // TRUE or FALSE}
```

The Image Presentation Rate/Stimulation Frequency is used to determine how often to present a new video image to the patient. The maximum effective rate can be 30 Hz if a Phillips video decoder is used as decoder. The host specifies how many frames to pad between video image frames. It can be configured for faster than 30 Hz, but this means a video frame is repeated.

unsigned short imageFrequencyPadding;

[The zoom setting for the video image capture can be set via the keypad.

unsigned short zoomSetting; //zoom in or zoom out

The device for capturing and transmitting video signals can be, for example, a video camera 112 (shown in FIGS. 6A-6B) that is mounted on a pair of glasses 5 (shown in FIGS. 5 and 6A-6B) suitable to be worn by a subject. The video camera 112 can capture the video signals in real time and transmit the video signals to the VPU 21. By way of example and not of limitation, the VPU 21 can perform one or more of digitizing the video signals, applying image-processing filters to the video signals, and downsampling resolution of the video signals to be suitable to the array of electrodes.

An exemplary retinal prosthesis system contains an array of sixty independently controlled electrodes implanted epiretinally. For instance, the array of electrodes can form a 6×10 grid of electrodes. In such a system, the video signal can be a sixty-pixel image or downsampled to a sixty-pixel image such that each pixel corresponds to one electrode. Each pixel in the sixty-pixel image is mapped to a stimulation amplitude to be applied to an electrode corresponding to the particular pixel. The mapping can be performed using look-up tables, which are generally customized for each subject. These customized look-up tables are built through experimental data obtained from each particular subject. The retinal prosthesis system contains memory for storage of the look-up table or tables obtained from experiments. Generally, the VPU 21 of the retinal prosthesis system contains memory for suitable for storage of these look-up table or tables.

Accordingly, what has been shown is an improved visual prosthesis with a remote driver and coil. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

It is to be understood that the disclosure is not limited to particular methods or systems, which can, of course, vary. For example, the person skilled in the art will understand that the number steps or components shown is only indicative and that the method can occur in more or fewer steps and that the system may contain more or less components according to the various embodiments. It is also to be understood that the terminology used herein is for the purpose of describing particular embodiments only, and is not intended to be limiting. As used in this specification and the appended claims, the singular forms "a", "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

A number of embodiments of the disclosure have been described. Nevertheless, it will be understood that various modifications may be made without departing from the spirit and scope of the present disclosure. Accordingly, other embodiments are within the scope of the following claims.

What we claim is:

1. A visual prosthesis comprising:
   a video processing unit configured to provide stimulation signals;
   a driver circuit configured to receive signals from the video processing unit including a power amplifier;
   an external coil driven by the power amplifier and configured to transmit the stimulation signals;
   a bidirectional radio frequency shielded link configured to connect the driver circuit to the external coil, through a tuning circuit, the bidirectional radio frequency shielded link, tuning circuit, and external coil configured to operate within a controlled environment test system, the controlled environment test system selected from a group consisting of magnetic resonance imaging, positron emission tomography, magnetoencephalography and electroencephalography, the driver circuit not configured to operate within the controlled environment test system, and the bidirectional radio frequency shielded link being long enough to separate the video processing unit and driver circuit from the controlled environment test system;
   an implantable neural stimulator configured to operate within the controlled environment test system, the controlled environment test system suitable for testing cortical responses and providing measurements of cortical responses; and
   an implantable coil electrically connected to the implantable neural stimulator configured to receive stimulation signals from the external coil.

2. The visual prosthesis according to claim 1, wherein the controlled environment is a magnetic resonance imaging field.

3. The visual prosthesis according to claim 1, wherein the controlled environment is a positron emission tomography field.

4. The visual prosthesis according to claim 1, wherein the controlled environment is a magnetoencephalography field.

5. The visual prosthesis according to claim 1, wherein the bidirectional radio frequency shielded link includes a coaxial cable.

6. The visual prosthesis according to claim 5, wherein the tuning circuit is between the coaxial cable and the external coil.

7. The visual prosthesis according to claim 6, wherein the tuning circuit includes a non-ferrite core inductor.

8. The visual prosthesis according to claim 1, further comprising a primary back telemetry coil electrically connected to the implantable neural stimulator and a secondary back telemetry coil electrically connected to the video processing unit through a second radio frequency shielded link.

9. The visual prosthesis according to claim 8, further comprising a low noise amplifier between the second radio frequency shielded link and the video processing unit.

10. The visual prosthesis according to claim 8, wherein the second radio frequency shielded link includes a coaxial cable.

11. A visual prosthesis comprising:
    a video processing unit configured to provide stimulation signals;
    a driver circuit configured to receive signals from the video processing unit including a power amplifier;
    an external coil driven by the power amplifier and configured to transmit the stimulation signals;
    a bidirectional radio frequency shielded link greater than one foot in length, the bidirectional radio frequency shielded link being long enough to connect the driver circuit to the external coil through a tuning circuit, the bidirectional radio frequency shielded link, tuning circuit, and external coil, configured to operate within a controlled environment test system, the controlled environment test system selected from a group consisting of magnetic resonance imaging, positron emission tomography, magnetoencephalography and electroencephalography, the driver circuit not configured to operate within the controlled environment test system;
    an implantable neural stimulator configured to operate within the controlled environment test system, the controlled environment test system suitable for testing cortical responses, and providing measurements of cortical responses;

an implantable coil electrically connected to the implantable neural stimulator configured to receive stimulation signals from the external coil.

12. The visual prosthesis according to claim 11, wherein the bidirectional radio frequency shielded link includes a coaxial cable.

13. The visual prosthesis according to claim 12, wherein the tuning circuit is between the coaxial cable and the external coil.

14. The visual prosthesis according to claim 13, wherein the tuning circuit includes a non-ferrite core inductor.

15. The visual prosthesis according to claim 11, further comprising a primary back telemetry coil electrically connected to the implantable neural stimulator and a secondary back telemetry coil electrically connected to the video processing unit through a second radio frequency shielded link.

16. The visual prosthesis according to claim 15, wherein the second radio frequency shielded link includes a coaxial cable.

17. The visual prosthesis according to claim 15, wherein the second radio frequency shielded link includes a tuning circuit between the coaxial cable and the secondary back telemetry coil.

18. The visual prosthesis according to claim 15, further comprising a low noise amplifier between the second radio frequency shielded link and the video processing unit.

19. The visual prosthesis according to claim 11, wherein the bidirectional radio frequency shielded link is greater than five feet in length.

20. The visual prosthesis according to claim 11, wherein the bidirectional radio frequency shielded link is greater than ten feet in length.

21. A method of fitting a visual prosthesis comprising providing a visual prosthesis according to claim 1;
    stimulating neural tissue;
    measuring cortical responses to the stimulation of neural tissue;
    adjusting the visual prosthesis according to the measurements of cortical responses.

22. The method according to claim 21, wherein the step of measuring cortical responses is measuring cortical responses with magnetic resonance imaging.

23. The method according to claim 21, wherein the step of measuring cortical responses is measuring cortical responses with positron emission tomography imaging.

24. The method according to claim 21, wherein the step of measuring cortical responses is measuring cortical responses with magnetoencephalography.

25. The method according to claim 21, wherein the step of measuring cortical responses is measuring cortical responses with electroencephalography.

* * * * *